United States Patent [19]

Cainelli et al.

[11] 4,435,575

[45] Mar. 6, 1984

[54] PROCESS FOR PREPARING CARBOXYLATED ORGANIC COMPOUNDS

[75] Inventors: Gianfranco Cainelli, Bologna; Marco Foa', Novara; Achille U. Ronchi, Ancona; Andrea Gardano, Trino Vercellese - Vercelli, all of Italy

[73] Assignee: Montedison S.p.A., Milan, Italy

[21] Appl. No.: 279,090

[22] Filed: Jun. 30, 1981

[30] Foreign Application Priority Data

Jul. 1, 1980 [IT] Italy ............................. 23163 A/80

[51] Int. Cl.³ .............................................. C07C 51/10
[52] U.S. Cl. ..................................... 546/341; 549/58; 549/71; 549/499; 260/413; 260/465.4; 560/97; 560/105; 560/114; 560/204; 560/206; 560/232; 562/406; 562/489; 562/497; 562/520
[58] Field of Search ............... 562/406, 489, 497, 520; 560/97, 204, 206, 232, 105, 114; 546/341; 549/71, 58; 260/347.4, 465.4, 413; 252/431 N, 462

[56] References Cited

U.S. PATENT DOCUMENTS

| | | | |
|---|---|---|---|
| 3,116,306 | 12/1963 | Heck | 260/410.9 |
| 3,708,529 | 1/1973 | Cassar et al. | 260/515 R |
| 4,128,572 | 12/1978 | Cassar et al. | 562/406 |
| 4,328,125 | 5/1982 | Drago et al. | 560/232 |

FOREIGN PATENT DOCUMENTS

| | | | |
|---|---|---|---|
| 822147 | 9/1969 | Canada | 260/485 |
| 2208878 | 6/1974 | France | . |
| 713515 | 8/1954 | United Kingdom | . |
| 1560609 | 2/1980 | United Kingdom | . |

OTHER PUBLICATIONS

Calmon et al., Ion Exchangers in Organic and Biochemistry, Interscience (1957), pp. 662-665.
Grubbs, Chemtech., 1977, pp. 512-518.
Nagy-Magos et al., J. of Organometallic Chem., 14 (1968), pp. 205-210.
Yermakov, Catal. Rev.-Sci. Eng., 13 (1), (1976), pp. 77-120.

Primary Examiner—John M. Ford
Assistant Examiner—Bernard Dentz

[57] ABSTRACT

A process is herein described for preparing carboxylated organic compounds (acids, esters, alkaline salts) of formula

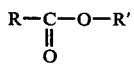

wherein R is a hydrocarbyl group having up to 11 carbon atoms (an aliphatic, alicyclic, aryl- or heteroarylalkyl group), also substituted, in its turn, by groups inert under the reaction conditions (alkyl, aryl, etheric, thioetheric, halogen, nitrile, ester, amide, ketonic groups), and R' is a hydrogen atom or an alkyl $C_1$-$C_8$ group, by reaction of carbon monoxide with the corresponding hydrocarbyl halides, having the halogen bound to a non-tertiary carbon atom, in the presence of catalysts which are salts of cobalt hydrocarbonyl, or precursors thereof, in a hydro-alcoholic or alcoholic solvent and in the presence of bases.

The process is characterized in that the catalytic system composed by the salt of cobalt hydrocarbonyl is supported on an anion exchange resin. The process permits to operate also continuously, in any case allowing an easy recovery, recycle and regeneration of the catalysts.

The products obtained, i.e. carboxylic acids, esters and alkaline salts thereof, are utilized as intermediates for organic syntheses particularly for fine chemistry (phytopharmaceuticals, pharmaceuticals, etc.).

19 Claims, No Drawings

PROCESS FOR PREPARING CARBOXYLATED ORGANIC COMPOUNDS

THE PRIOR ART

There are known several methods for synthetically preparing the acids and/or esters and salts of the present invention. For example, aryl- and heteroaryl-acetic esters can be prepared by reacting aryl- or heteroaryl chloromethylderivatives with alkaline cyanides and by subsequent hydrolysis of the resulting nitrile in an alcoholic medium. Otherwise they can be obtained according to the known Willgerodt reaction: for example, preparation of the alpha-thienylacetic acid is effected by reacting 2-acetylthiophene with ammonium polysulphide to obtain alpha-thienylthioacetamide, which is then saponified to alpha-thienylacetic acid.

These methods are multistage non-catalytic methods essentially complicated owing to use of reagents not easily available and/or difficult to handle (cyanides) with the relevant operating (environmental pollution) and economic burdens which render them of little interest from an industrial viewpoint.

On the other hand it is known to use, for obtaining phenyl- and thienyl-acetic compounds, catalytic systems based on metal-carbonyl complexes (Ni, Co, Rh) in the carbonylation of benzyl halides or of thienyl halides in an alkaline medium to obtain the corresponding esters and/or acids.

These processes, however, exhibit several drawbacks which mainly consist in the use of expensive catalysts, or in the necessity of separately preparing the catalyst under conditions different from those of the synthesis; in the unsatisfactory reaction yields and rates and in the use of special solvents.

It is known for example that it is possible to prepare carboxylated compounds starting from the corresponding halides by reaction with carbon monoxide in the presence of alkaline salts of cobalt hydrocarbonyl and of ferro-dihydro-carbonyl. Such process, however, is characterized by low yields of carbonylation product and by a low catalytic activity, and it requires a separate preparation of the catalytic system.

There was also disclosed the preparation of phenylacetic acid and of aryl- and heteroaryl-acetic esters in which the carbonylation of the corresponding halides is carried out in the presence of a catalyst system prepared "in situ" from a Co salt, a Mn-Fe alloy (about 80% of finely grounded Mn), and sulphurated activators such as sodium sulphide and thiosulphide, in an hydroalcoholic or alcoholic medium in the presence of a basic system such as CaO, NaOH, KOH, $Na_2CO_3$ and $K_2CO_3$ respectively.

Such processes, although characterized by high yields and by a good catalyst activity, exhibit the drawback of not allowing a recovery of the catalytic complex at the end of the reaction, of requiring processes for recovering the Co from the exhausted catalyst which are not always simple and which, above all, are little suitable for a continuous operating cycle.

Some of these drawbacks have been partially overcome by applying the phase transfer technique to the carboxylation reactions of organic halides.

OBJECTS OF THE INVENTION

The present invention relates to a process for preparing carboxylated organic compounds.

In particular it relates to an improved process for preparing carboxylic acids and/or esters and alkaline salts thereof.

Even more particularly this invention relates to a process for preparing acid carboxylated organic compounds, acids, carboxylic salts and/or esters and alkaline salts thereof, by reaction of the corresponding organic halides and carbon monoxide in the presence of a catalytic system based on carbonyl complexes of cobalt.

From the alkaline salts and/or from the esters the acid is easily obtainable by acidification, hydrolysis etc. according to conventional methods.

To the carboxylated organic compounds prepared according to this invention, the following general formula is ascribable (I):

wherein R is a hydrocarbyl group having up to 11 carbon atoms selected from the aliphatic, alicyclic, aryl- and heteroaryl-alkyl radicals and R' is a hydrogen atom or an alkyl group having up to 8 carbon atoms.

Said groups, in their turn, may be substituted by groups which are inert under the reaction conditions; suitable groups are, for example, the alkyl, aryl, etheric, thioetheric, nitrile, ester, halogen, amide, ketonic groups etc.

The hetero-aryl-alkyl R groups may contain atoms of O, N, S.

The resulting carboxylated compounds, acids and esters or alkaline salts, are interesting products having useful utilizations in a wide range of industrial applications. In fact they represent active intermediates for organic syntheses in general, with particular possibilities in the field of fine chemistry, of phytopharmaceuticals, of pharmaceuticals etc. Possible conventional applications are represented by the use of the esters as solvents, plasticizers for synthetic and natural plastic materials, surfactants, etc.

For example, the esters of malonic acid are employed as intermediates in the pharmaceutical field (barbiturics) and in the one in which use of a substance imparting an aromatic taste or odor is indicated. The esters of phenylacetic acid, prepared according to the present invention, find a well defined and important application in the field of perfumes (phenylethyl phenylacetate, benzyl phenylacetate, etc.). Respectively, the corresponding acid (phenylacetic acid) is employed in the field of pesticides, such as the ethyl ester of the dimethyl-dithiophosphoryl-phenylacetic acid, which is known under the trade name CIDIAL, and in the pharmaceutical field (penicillins).

The alpha-thienylacetic acid is utilized, in its turn, in the preparation of compound suited to protect the vegetable cultivations (wheat, cereals) from the damages caused by herbicides, or in the preparation of pharmaceuticals, such as antibiotics in general, for instance in the preparation of cephalotine, which is the sodium salt of 7-(thiophene-2-acetamido)-cephalosporanic acid.

Thus it is an object of the present invention to provide a simple and economic process for preparing, on a commercial scale, the carboxylic organic compounds of formula (I), acids, esters and/or alkaline salts, which is free from the drawbacks cited with regard to the prior art taken into examination, and which offers in particular the possibility of operating continuously, allowing an easy recovery and recycle of the catalyst, which is made possible by the non-homogeneity of the reaction medium.

In fact, according to the present invention, a process is provided for preparing carboxylic organic compounds of formula (I) by synthesis from carbon monoxide and from the corresponding organic halides in a hydro-alcoholic or basic alcoholic medium, in the presence of a catalytic system based on cobalt carbonyl complexes supported on an anion exchange resin, better defined below.

In fact, we have ascertained that the method of preparing carboxylated organic compounds (I) by carbonylation of halogen derivatives can be further improved as regards both the recovery and recycle of the catalyst, at the end of the productive cycle, and the recovery of the Co in the exhausted catalyst, renderering possible also the transfer of such technique to a "continuous" process, not really feasible till now. In fact, the catalyst, composed by a salt of cobalt hydrocarbonyl, is carried on an anion exchange resin, maintaining practically the same high yields and selectivities achieved by the process when conducted in a homogeneous phase according to the art.

These and still other objects and advantages, will more clearly appear to those skilled in the art from the following description.

GENERAL DESCRIPTION OF THE INVENTION

According to this invention, there is provided a process for preparing carboxylated organic compounds having formula (I), by reacting the corresponding organic halides of formula (II):

$$R-X \qquad (II)$$

in which R has the meaning already defined and X is a halide selected from Cl, Br and I, said halide being bound to a primary or secondary carbon atom, with carbon monoxide in the presence of a salt of cobalt hydrocarbonyl, in a hydro-alcoholic or alcoholic solvent and in the presence of bases, characterized in that the catalyst system is composed by a salt of cobalt hydrocarbonyl supported on an anion exchange resin (basic).

The reaction may be schematically represented by the following equations:

$$R-X + CO + R'OH + B \xrightarrow[H_2O/alcohol]{cat.\ resin} \qquad (1)$$

$$R-\underset{\underset{O}{\|}}{C}-O-R' + BHX$$

wherein R, R' and X have the meanings previously defined hereinabove, B is a basic substance as defined below.

$$R-X + CO + 2MOH \xrightarrow[H_2O/alcohol]{cat.\ resin} \qquad (2)$$

$$R-\underset{\underset{O}{\|}}{C}-O-M + MX + H_2O$$

wherein the symbols have the same meanings as specified hereinabove, and M is an alkaline metal or an alkaline-earth metal, preferably selected from Na, K, Ca.

The free carboxylic acid is then easily obtained from the esters (reaction 1) or from the alkaline salts (reaction 2) by hydrolysis or by shifting with strong acids (HCl, $H_2SO_4$), extraction with solvents, etc., according to conventional techniques.

From reactions (1) and (2) it is evident that they can be selectively applied to the preparation of the alkaline salts and alkyl esters as a function of the type and/or amount of base B and MOH which are employed.

Effective resins used as the carrier for the catalyst based on the salt of the cobalt hydrocarbonyl are the resins having preferably a styrene, acrylic matrix, or the polycondensation resins.

These are characterized by the presence of at least a strongly basic functional group of formula (III) and (IV):

$$-CH_2-N^+(CH_3)_3X^-;\ -CH_2N^+-(CH_3)_2X^-$$
$$\qquad\qquad\qquad\qquad\qquad\quad |$$
$$\qquad\qquad\qquad\qquad\qquad CH_2CH_2OH$$
$$\quad (III) \qquad\qquad\quad (IV)$$

or moderately basic group of formula (V):

$$-CH_2-N(CH_3)_2 \qquad\qquad (V)$$

in which X has the meaning already specified.

Furthermore, the resins may be either of the gel type or of the porous, isoporous and microporous type. The following resins have proved particularly effective: AMBERLITE A 26 (III), A 27 (III), A 29 (IV); AMBERLITE IRA 402 (III) and IRA 93 (V) (trade-marks of Messrs Rohm & Haas); KASTEL A 101 (V) and A500P (III) (trade-marks of Montedison S.p.A.).

The catalysts are in themselves conventional in the carbonylation reactions described hereinabove and are salts of cobalt hydrocarbonyl corresponding to the formula:

$$Me^{n+}[Co(CO)_4]_n \qquad\qquad (VI)$$

in which Me is a cation of a metal having valence n, such as the alkaline metals (Na, K, Li) or cobalt, iron, manganese, etc. which are known and preparable according to conventional techniques.

Preferred catalysts are the salts of sodium, cobalt, manganese and iron of formula (VI).

The catalyst based on the salt of cobalt hydrocarbonyl is preferably prepared, according to this invention, from a cobalt salt, such as for example chloride, sulphide, bromide salt, etc., a Fe-Mn alloy (containing about 80% of Mn) and from sulphurated promoters, in the desired alcohol (such as methyl, ethyl alcohol, etc.), at a carbon monoxide pressure ranging from 1 to 20 atm. and at temperatures in the range of from 10° to 80° C., preferably of from 25° to 35° C., approximately.

The cobalt salt concentration in the solution is comprised between 0.3 and 1 mole/liter. For each mole of cobalt salt there are employed from 1 to 2 moles of Mn in the form of a Fe/Mn alloy. The Fe/Mn alloy is previously ground so as it passes through a screen of at least 5,000 meshes/cm².

The preferred sulphurated promoters are sodium sulphide and thiosulphide which are employed in amounts of from 0.01 to 0.1 moles per mole of cobalt salt.

The alcoholic mixture containing the cobalt salt, the alloy and the sulphurated promoter in the alcoholic solvent is maintained in a CO atmosphere under intense stirring for a time-period sufficient to complete the CO absorption, such time-period being of at least 2-3 hours. Salts of Mn and/or of Fe of cobalt hydrocarbonyl are thus obtained.

As an alternative, the catalyst based on the cobalt salt of the Co hydrocarbonyl may be prepared from $Co_2(CO)_8$ by the dismutation reaction in an alcoholic and preferably basic medium, or the sodium salt may be prepared from $Co_2(CO)_8$ by reduction with a sodium amalgam in an etheric solvent (tetrahydrofuran).

Conversely, $Co_2(CO)_8$ is prepared for example from $CoCO_3$ under CO and hydrogen pressure in petroleum ether.

Carrying of the catalyst occurs very simply by contacting the resin, optionally washed with an alcohol (methyl or ethyl alcohol), the same alcohol used in the reaction, for eliminating the humidity contained in said resin, with an alcoholic solution (of methyl or ethyl alcohol) of the catalyst previously prepared. Contacting occurs for example by immersing the resin in the catalytic solution.

The resin is employed at least in a stoichiometric amount (calculated on the equivalents/g groups) in respect of the catalyst amount, in such a way that, after a short contact time, the catalyst itself is throughly carried on the resin.

The check is provided by the absence of $Co(CO)_4^-$—ions revealed by the solution subjected to infrared analysis, and by the presence of said ions in the polymeric matrix. Time-periods in the order of 15 minutes to 1 hour approximately are generally sufficient.

The carbonylation reaction is conducted in a substantially conventional manner, i.e. in an aqueous alcohol solvent with an alcohol/$H_2O$ ratio up to about 20% by volume of $H_2O$, when the acids and/or their alkaline salts of formula (I) (equation 1) are to be prepared, and preferably in an anhydrous alcoholic solvent when the esters of formula (I) (equation 2) are to be obtained.

Effective alcohols have proved to be the methyl, ethyl, isopropyl, butyl etc. alcohols.

The reaction is carried out in the presence of a mineral or organic basic agent.

Effective mineral bases have proved to be the alkaline and alkaline-earth oxides and hydroxides, the alkaline and alkaline-earth carbonates, the alkaline bicarbonates, the alcoholates, the tertiary amines etc.

With reference to equations (1) and (2), the molar ratio between basic compound B or MOH, defined hereinabove, and the halide (II) must be at least equal to the stoichiometric one. In particular, the use of the alkaline hydroxides, which are additioned in an aqueous solution from 5 to 50% by weight, requires that they should be gradually added on the basis of an accurate adjustment of the pH value, which must approximately in the range from 8.5 to 9.5 about in order to obtain prevailingly esters, and from about 10 to about 11.5 to obtain the alkaline salts of the acids.

The calcium hydrate and the oxide may be added one time only. The use of alcoholates as bases is limited to the synthesis of esters and requires also an accurate regulation of the pH. The use of carbonates and bicarbonates is suitable for the preparation of esters and does not require any pH regulation. A suitable tertiary amine is, for example, dicyclohexyl-ethylamine, etc. The resin-supported catalyst is added in an amount approximately ranging from 1:10 to 1:500 in respect of the halide of formula (II), and calculated as moles of metal cobalt per moles of halide (II).

The carbonylation reaction is carried out by contacting the resin containing the catalyst with the alkaline solution containing the halide (II) and the base in a carbon monoxide atmosphere.

The halide (II) is added, according to the case, either gradually or all at once, and its concentration in the solvent ranges approximately from 10 to 40% by weight.

The temperature is approximately comprised between 20° and 90° C., preferably between 30° and 70° C., approximately.

The carbon monoxide pressure varies approximately from 1 to 60 atm., depending on the organic substrate to be carbonylated.

A time ranging from 2 to 24 hours is required to complete the reaction, depending on the parameters used and on the organic substrate used considered.

At the end of the reaction, the resin is separated by simple filtration. The resin so separated can be utilized for a successive carbonylation reaction, optionally after having regenerated the exhausted catalyst. The resin regeneration is effected after a certain number of cycles, when practically all the supported catalyst is exhausted, simply by washing with an aqueous solution of hydrochloric acid. In such manner practically all the cobalt passes into the aqueous solution and the resin, separated by filtration from the acid solution, washed with water and alcohol, is ready for being used again as carrier for the catalyst.

The following halides (II) have proved to be effective: methyl chloroacetate, ethyl chloroacetate, chloroacetonitrile, benzyl chloride, benzyl bromide, methyl-, methoxy-, chloro-, bromo-, cyano-, carboethoxy-substituted benzyl chloride, alpha-chloromethyl-naphthalene, alpha, alpha'-dichloro-xylene, chloro-ethylbenzene, methyl- or ethyl alpha-bromo-phenyl-acetate, 2-chloro-methyl-thiophene, 2-chloro-methyl-furan, 3-chloromethyl-benzothiophene, 3-chloromethyl-pyridine, chloroacetone, iodooctane, etc.

The separation of the reaction products from the organic mixture, after recovery of the resin, is carried out according to conventional techniques: for example, after filtration of the inorganic salts, by fractional distillation of the ester (I) from which the acid is obtainable by conventional hydrolysis; or, after separation of the resin (filtration), recovery of the solvent (distillation), extraction with a solvent (ether) of the alkaline aqueous solution containing the alkaline salt of the acid, in order to remove the neutral fraction, by acidification (HCl etc.) and extraction, with a solvent, of the released acid, which is then purified, if necessary, etc.

According to a practical procedure, the invention can be practiced as follows.

In a reactor, equipped with a stirrer, a temperature regulating system and a reagent inlet system, the catalyst, freshly prepared separately and supported on the resin, is added, under a carbon monoxide head, to the solvent in the desired ratio. The suspension so obtained is then stirred. Subsequently, always under a carbon monoxide head, the base is added in an at least equimolar amount in respect of the halide (II), and the halide (II) in the desired ratios.

CO, in a high stoichiometric excess, is further fed, at the desired pressure and temperature, under stirring, for a few hours, until the conclusion of the CO absorption is observed.

At the end of the CO absorption, the reaction mixture is treated with a view to separating the products, employing the aforesaid conventional techniques.

The process, due to the mild operating conditions, appears particularly advantageous especially because it is possible to operate continuously with an easy recovery, regeneration and recycle of the catalytic system.

SPECIFIC DESCRIPTION OF THE INVENTION

The following examples are given merely for illustrating the present invention.

EXAMPLE 1

Into a 500-ml flask, equipped with a mechanical agitator, a reflux cooler connected with a Mariotte bottle containing CO, with a filtering septum and a probe for measuring the pH, there were introduced, under a CO head: 100 ml of methanol, 10 ml of a catalyst solution (2.2 g of Co as cobaltate, $Co(CO)_4-$, per 100 ml) prepared from 20 g of $CoCl_2.6H_2O$, 0.6 g of $Na_2S.9H_2O$, 1.5 g of $Na_2S_2O_3.5H_2O$, 10 g of Mn/Fe alloy in powder passing through a 5000 meshes/cm$^2$ screen, 180 ml of $CH_3OH$, and carbon monoxide at ambient pressure till conclusion of the CO absorption. To the catalyst solution so obtained there were then added 7 g of resin AMBERLYST A 26 type (III), previously washed with methanol and dried in the reaction flask. The suspension was stirred at room temperature for 15 minutes in order to thoroughly support the catalyst on the resin (disappearance of the IR band, typical of the cobaltate, in the methanol solution). After addition of 10 ml of $H_2O$, the temperature was brought to 55°–56° C. and in 4 hours 44 g of benzyl chloride were added, maintaining the pH at a value of 10.5–11 by addition of an aqueous solution of NaOH at 30% by weight.

After about 2 hours from the conclusion of the addition, the reaction was concluded (CO absorption stopped). The mixture was cooled down to room temperature and filtered from the resin. Now into the flash there were introduced 100 ml of $CH_3OH$, 4 ml of the catalyst solution and, after stirring at room temperature for 15 minutes, another carbonylation cycle of 44 g of benzyl chloride was carried out according to the modalities specified hereinabove. At the end of the second cycle the reaction mixture was filtered and the filtrate was combined with the one of the first cycle.

Water acidulated with HCl was then added and the whole was extracted in ethyl ether. The etheric extract was washed with an aqueous solution of $NaHCO_3$. The alkaline solution so obtained was acidified again and extracted with ethyl ether.

By evaporating the extraction ether there were obtained 82.4 g of phenylacetic acid corresponding to a yield of 87.1% referred to the benzyl chloride employed.

The recovered resin was suspended in water acidulated with HCl and it was stirred for 30 minutes at room temperature and then filtered and washed with water and methanol. After this treatment it was possible to utilize it again for a successive cycle.

The Co content in the filtration water was equal to 0.3 g (quantitative value).

EXAMPLE 2

The operation was according to the modalities and in the equipment described in Example 1.

After the first carbonylation cycle the second cycle was conducted without any further addition of catalyst.

From the treatment of the filtrates it was possible to obtain 74 g of phenylacetic acid, corresponding to a yield of 78% referred to the benzyl chloride introduced.

This example proves that the catalyst employed is recoverable, after a productive cycle, still in activated form (cobaltate).

EXAMPLE 3

Into the equipment of Example 1 there were introduced, under a CO head, 150 ml of $C_2H_5OH$, 0.75 g of $NaCo(CO)_4$, prepared from $Co_2(CO)_8$ and sodium amalgam, and 7 g of AMBERLYST A 26, type (III), washed with ethyl alcohol. It was stirred at room temperature for 15 minutes until disappearance of the IR band in the alcoholic solution, which is typical of the anion cobaltate. The temperature was then brought to 47° C., whereupon 52 g of $K_2CO_3$ and, in 8 hours, 44 g of benzyl chloride were added. The reaction mixture was stirred for a total time of 16 hours at 47° C.

At the end of the reaction it was filtered and the filtrate was distilled under vacuum (20 mm Hg of residual vacuum), so recovering 37 g of ethyl phenylacetate (yield=65% referred to the benzyl chloride introduced).

The resin, after washing with acidulated water and with ethyl alcohol, was employable again for a consecutive cycle. Analogous results were obtained by substituting $NaCo(CO)_4$ by an equivalent amount of $Co_2(CO)_8$.

EXAMPLE 4

Into the equipment of Example 1, there were introduced, under a CO head: 100 ml of methanol, 10 ml of a catalyst solution prepared as in Example 1, and 7 g of resin KASTEL A 101, type (V). It was stirred for 15 minutes in order to completely support the catalyst.

According to the modalities described in Example 1, 44 g of benzyl chloride were carbonylated.

The solution filtered from the resin at the end of the test was treated as described in Example 1, thus obtaining 43 g of phenylacetic acid (yield=91% referred to the benzyl chloride introduced).

EXAMPLE 5

The operation was carried out in the same equipment and according to the same modalities as in Example 1.

Under a CO head, there were charged 100 ml of $CH_3OH$, 10 ml of catalyst solution prepared as in Example 1, and 7 g of resin AMBERLYST A 27 type (III). It was stirred for 15 minutes whereupon operating as in Example 1, 44 g of benzyl chloride were carbonylated.

The solution filtered from the resin at the end of the test was treated as described in Example 1, thus obtaining 39.3 g of phenylacetic acid (yield=83%).

EXAMPLE 6

The operation was carried out in the same equipment and with the same modalities as in Example 1.

100 ml of $CH_3OH$, 10 ml of a catalyst solution prepared as in Example 1 and 7 g of resin AMBERLYST A 29 type (IV) were charged under a CO head. The whole was stirred for 15 minutes, whereupon operating as in Example 1, 44 g of benzyl chloride were carbonylated.

The solution filtered from the resin at the end of the test was treated as described in Example 1, thus obtaining 38.6 g of phenylacetic acid (yield: 81.6%).

EXAMPLE 7

The operation was carried out in the same equipment and with the same modalities as in Example 1.

100 ml of $CH_3OH$, 10 ml of a catalyst solution (2.2 g of Co as cobaltate for 100 ml) and 7 g of AMBERLITE IRA 402 type (III) were charged under a CO head. It was left under stirring for 15 minutes whereupon operating as in Example 1, 44 g of benzyl chloride were carbonylated.

The solution filtered from the resin at the end of the test was treated as described in Example 1, so obtaining 36.8 g of phenylacetic acid (yield=77.8%).

EXAMPLE 8

Into a flask, under stirring and under a $N_2$ head, there were introduced 130 ml of anhydrous ethyl alcohol, 22 ml of a solution of catalyst prepared from 20 g of $CoCl_2.6H_2O$, 0.6 g of $Na_2S.9H_2O$, 1.5 g of $Na_2S_2O_3.5H_2O$, 10 g of Mn/Fe alloy, 180 ml of $C_2H_5OH$, as described in Example 1. There were then added 7 g of resin AMBERLYST A 26 type (III), previously washed with ethyl alcohol and dried.

The whole was left stirring at room temperature for 15 minutes, checking, by IR analysis, the disappearance from the solution of the band typical of cobaltate.

The suspension was additioned with 2 ml of $H_2O$ and was introduced into a 1 liter autoclave under a $N_2$ head.

62 g of ethyl chloroacetate and 53 g of $Na_2CO_3$ were then added. The autoclave was washed with CO and 15 atm. thereof were charged. The temperature was brought to 70° C. and it was left under stirring at such temperature for 10 hours, maintaining a pressure of 15 atm. by successively and repeatedly charging CO. At the end of the test it was filtered and the filtrate was distilled under vacuum thus recovering 65.9 g of diethyl-malonate (yield=81.4%).

The resin, washed with acidulated water and successively with ethyl alcohol, was employable for a successive cycle.

EXAMPLE 9

100 ml of $CH_3OH$, 7 g of AMBERLYST A 26 type (III) and 0.75 g of $NaCo(CO)_4$ were introduced into the equipment of Example 1. It was left under stirring for 15 minutes whereupon 10 ml of $H_2O$ were added. Successively, maintaining the pH at a value of from 10.5 to 11 with a NaOH solution at 30%, 9 g of 2-chloromethylfuran were dropped in 2 hours at a temperature of 25°–30° C. At the end of the reaction, it was filtered from the resin and by operating as described in Example 1, 5.6 g of 2-furanacetic acid were isolated (yield=57% referred to the starting product).

What is claimed is:

1. A catalytic process for preparing carboxylated organic compounds, acids and/or esters and/or alkaline salts having the formula (I)

$$R-\underset{\underset{O}{\|}}{C}-O-R' \qquad (I)$$

wherein R is a hydrocarbyl group having up to 11 carbon atoms, selected from the aliphatic alicyclic, aryl- and heteroarylalkyl groups, and said groups substituted by substituents selected from the group consisting of alkyl, aryl, etheric, thioetheric, halogen, nitrile, ester, amide and ketonic groups, and R' is a hydrogen atom or an alkyl group having up to 8 carbon atoms, by reacting with carbon monoxide the corresponding halides of formula (II)

$$R-X \qquad (II)$$

wherein R has the same meaning as in formula (I) and X is a halogen bound to a primary or secondary carbon atom, and selected from the group consisting of Cl, Br and I, in the presence of a salt of cobalt hydrocarbonyl in an alcoholic or aqueous alcoholic solvent and of bases, characterized in that the catalyst is a salt of cobalt hydrocarbonyl having the formula:

$$Me^{n+}[Co(CO)_4]_n$$

in which Me is a cation of a metal having a valence n, selected from the group consisting of Na, K, Li, Co, Fe, and Mn, said catalyst being supported on an anion exchange resin.

2. A process according to claim 1, characterized in that the catalyst is one in which the cobalt hydrocarbonyl salt is supported on a resin selected from those having a styrene matrix, an acrylic matrix, or from the polycondensation resins, further characterized by the presence of at least a functional group selected from:

$$-CH_2-N^+(CH_3)_3X^-; \quad -CH_2N^+-(CH_3)_2X^-; \quad -CH_2-N(CH_3)_2.$$
$$\qquad\qquad\qquad\qquad\qquad\quad |$$
$$\qquad\qquad\qquad\qquad\quad CH_2CH_2OH$$
$$(III) \qquad\qquad\qquad (IV) \qquad\qquad\qquad (V)$$

3. A process according to claim 2, characterized in that the resin is selected from the gel-type, porous, isoporous and macroporous resins.

4. A process according to claim 2, characterized in that the resin is selected from the group consisting of: AMBERLIST A 26, AMBERLYST A 27, AMBERLYST A 29, AMBERLITE IRA 402, AMBERLITE IRA 93, KASTEL A 101 and KASTEL A 500 P.

5. A process according to claim 1, characterized in that the resin is employed in an at least stoichiometric amount calculated with reference to the equivalent groups per gram, in respect of the amount of catalyst based on cobalt hydrocarbonyl salt.

6. A process according to claim 1, characterized in that the catalytic, cobalt hydrocarbonyl salt, is supported on the resin by contacting the latter with a solution thereof in an alcohol or an aqueous-alcohol.

7. A process according to claim 1, characterized in that the catalytic cobalt hydrocarbonyl salt, is added in amounts of from 1:10 to 1:500, approximately, calculated as cobalt moles in respect of the moles of halide (II).

8. A process according to claim 1, characterized in that it is conducted in an alcoholic or aqueous-alcoholic solvent.

9. A process according to claim 1, characterized in that the base is selected from the group consisting of alkaline and alkaline-earth oxides, hydroxides, carbonates, bicarbonates, alkaline alcoholates and tertiary amines.

10. A process according to claim 9, characterized in that the base is employed in an least stoichiometric ratio in respect of the halide (II).

11. A process according to claim 1, characterized in that the reaction is conducted at a pH ranging from 8.5 to 9.5 approximately, in order to prevailingly obtain the esters of the carboxylic acids.

12. A process according to claim 1, characterized in that the reaction is conducted at a pH ranging from 10 to 11.5 in order to obtain the alkaline salts of the carboxylic acids.

13. A process according to claim 1, characterized in that it is conducted at temperatures approximately ranging from 20° to 90° C., at a pressure from 1 to 60 atm., approximately.

14. A process according to claim 1, characterized in that the starting halide of formula (II), defined in claim 1, is selected from the group consisting of methyl- and ethylchloro-acetate, chloro-acetonitrile, benzyl chloride, benzyl bromide, methyl-, methoxy-, chloro-, bromo-, cyano-, and carboethoxy-substituted benzyl chloride, alpha-chloromethyl-naphthalene, alpha-alpha'-dichloro-xylene, chloro-ethylbenzene, methyl- or ethyl alpha-bromo-phenylacetate, 2-chloro-methyl-thiophene, 2-chloro-methylfuran, 3-chloro-methyl-benzothiophene, 3-chloro-methylpyridine, chloro-acteone, and iodooctane.

15. A process according to claim 1, characterized in that the catalytic cobalt hydrocarbonyl salt is prepared by reaction of CO and a cobalt salt, a Fe-Mn alloy containing about 80% of Mn, and a sulphurated promoter, in the alcoholic solvent, at a pressure of from 1 to 20 atmospheres and at a temperature ranging from about 10° C. to about 80° C.

16. The process of claim 15 in which the cobalt salt reacted with the CO is selected from the group consisting of the chlorides, bromides and sulphides.

17. The process of claim 15, in which the sulphurated promoter is selected from the group consisting of alkaline sulphides and thiosulphides.

18. The process of claim 1, in which the alcoholic solvent is selected from the group consisting of methyl, ethyl, isopropyl and butyl alcohol, and said alcohols containing up to about 20% of water by volume.

19. The process of claim 1, in which the reaction is carried out at a temperature ranging from about 30° C. to about 70° C.

* * * * *